United States Patent [19]

Heijnen

[11] Patent Number: 4,560,479
[45] Date of Patent: Dec. 24, 1985

[54] PROCESS FOR PREPARING BIOMASS ATTACHED TO A CARRIER

[75] Inventor: Joseph J. Heijnen, 's-Gravenhage, Netherlands

[73] Assignee: Gist-Brocades N.V., Delft, Netherlands

[21] Appl. No.: 461,635

[22] Filed: Jan. 27, 1983

Related U.S. Application Data

[63] Continuation-in-part of Ser. No. 182,068, Aug. 28, 1980, abandoned.

[30] Foreign Application Priority Data

Nov. 7, 1979 [NL] Netherlands ............... 7908138

[51] Int. Cl.$^4$ ................. C02F 3/06; C02F 3/28; C12P 5/02
[52] U.S. Cl. .................... 210/603; 210/617; 210/150; 210/903; 435/167; 435/170; 435/174; 435/801
[58] Field of Search ............ 210/603, 617, 618, 903, 210/150, 151; 435/170, 171, 174, 177, 178, 167, 813, 804, 801; 48/197 A

[56] References Cited

U.S. PATENT DOCUMENTS

| | | | |
|---|---|---|---|
| 3,846,289 | 11/1974 | Jeris et al. | 210/903 |
| 4,009,099 | 2/1977 | Jeris | 210/903 |
| 4,225,430 | 9/1980 | Bosman | 210/618 |
| 4,255,266 | 3/1981 | Moreaud et al. | 210/617 |
| 4,284,508 | 8/1981 | Jewell | 210/603 |
| 4,419,243 | 12/1983 | Atkinson et al. | 210/618 |

OTHER PUBLICATIONS

Atkinson, et al.; "The Completely Mixed Microbial Film Fermenter"; Trans. Inst. Chem. Engrs., vol. 50, 1972 (pp. 208–216).

Jack et al., "The Immobilization of Whole Cells"; Advances in Biochem. Eng., vol. 5, 1977 (pp. 126–127).

*Primary Examiner*—Benoit Castel
*Attorney, Agent, or Firm*—Bierman, Peroff & Muserlian

[57] ABSTRACT

In a process for the production and maintenance of well-adhering biomass attached to carrier particles capable of decomposing contaminants in waste water containing both well-adhering and non-adhering microorganisms wherein a granular carrier is contacted in a reaction space with a continuous stream of waste water containing both well-adhering and non-adhering microorganisms and nutrients for the growth and the maintenance of the microorganisms in an adherent layer until a sufficiently thick, well-adhering layer of microorganisms is formed and maintained on the carrier, the improvement comprising maintaining the residence time of the waste water in the reaction space lower than the reciprocal maximum growth rate of the microorganisms on carrier particles of at least 0.1 mm while generating in the reaction liquid shear forces caused by liquid motion and circulation caused by gas bubbles and washing out of the reaction space all non-adhering microorganisms.

The process can be used for the production of high amounts per cubic meter of reactor volume of all kinds of biomass attached to a carrier, e.g. biomasses as are applied in the biological purification of waste water, aerobic biomass, anaerobic biomass, nitrifying biomass and denitrifying biomass, as well as biomasses forming a desired metabolic product which inhibits its own production rate at higher concentrations, e.g. biomass for the production of alcohol.

18 Claims, 4 Drawing Figures

PROCESS FOR PREPARING BIOMASS ATTACHED TO A CARRIER

PRIOR APPLICATION

This application is a continuation-in-part of my copending, commonly assigned U.S. patent application Ser. No. 182,068 filed Aug. 28, 1980, now abandoned.

STATE OF THE ART

In all kinds of biological processes, water which contains nutrients is contacted with microorganisms (so-called biomass) with the biomass converting the nutrients present in the water. Important processes of this type e.g. are processes for the biological purification of waste water and processes wherein the microorganisms involved excrete a desired product as a metabolite. In the processes used for the purification of waste water, the conversion rate (speed by which the nutrients present in the waste water are converted) calculated per cubic meter of reactor space is low because the biomass concentration, which can be reached in the reactor, is low.

This is the case in biological aerobic processes for COD removal from waste water in a continuous reactor, biological aerobic nitrification processes in a continuous reactor, biological anaerobic processes for the removal of COD from waste water in a continuous reactor and biological anaerobic denitrification processes in a continuous reactor. Typical biomass concentrations are 1–3 kg/m$^3$ and typical conversion rates are 0.1–3 kg COD/m$^3$ per day. The low level of biomass concentration in these processes is due to the very low settling velocity of microorganisms, by which a discharge of these microorganisms takes place from a continuous reactor continuously.

In practice, these microorganisms washed away from the reactor are separated as much as possible by settling, filtration, or centrifugation and subsequently are returned to the reactor. However, these separation technics are expensive (centrifuge) or have their own specific restrictions (e.g. floating sludge in the settling tank) and higher biomass concentrations than the mentioned ones are not obtained. Also in some processes, wherein the microorganisms form a desired metabolic product which at higher concentrations inhibits its own rate of production, the conversion per cubic meter of reactor volume is low. An example is the production of ethanol from carbohydrates and the inhibition leads to low conversion rates per kg of biomass. High conversion rates per cubic meter of reactor space then only can be obtained by increasing the biomass concentration in the reactor.

From the foregoing, it is clear that obtaining a high biomass concentration is necessary to reach high conversion rates in biological processes. A very promsing method for obtaining a high biomass concentration is attaching biomass to a carrier. Such a carrier grown with biomass has a high sedimentation rate if the specific weight of the carrier is sufficiently high. If the settling rate of the carrier grown with biomass is higher than the liquid rate at the reactor outlet, the biomass is not all washed away. However, high demands are made upon the adhesion of biomass to such a carrier.

To actually obtain a high conversion rate, other factors which are important for the conversion should not form an impediment. Thus, in the aerobic purification of waste water at a high biomass concentration, oxygen should be transferred much quicker and in the anaerobic purification of waste water, methane and carbon dioxide should be carried out much quicker. The variations in pH, substrate concentrations, temperature or concentration of toxic substances of a waste water which is introduced into the reactor should be smoothed out much quicker by adequate mixing of the liquid. This can only be obtained by dispering a sufficiently large amount of mechanical energy in the reactor which entails the generation of high shearing forces in the reactor.

The adhesion of biomass to a carrier now should be such that the biomass still adheres to the carrier under conditions of high shearing forces. The adhesion of biomass to surfaces is a process which is not well understood and a survey of the knowledge in this field is to be found in K. C. Marshall "The effect of surfaces on microbial activity", Water Pollution Microbiology Vol. 2 (1978), p. 51.

A distinction is made between (1) adhesion of biomass to surfaces by weak forces such as electrostatic, Van der Waals and hydrophobic inert actions. This adhesion of biomass is so weak, that it is already disturbed by weak shearing forces such as appear in running aerated water. The same forces affect the flocculation of microorganisms, see C. W. C. Gregor et al "Factors affecting the flocculation of bacteria by chemical additives", Biot. en Bioeng., Vol. 11 (1969) p. 127 and M. W. Tenny et al., "Chemical and autoflocculation of microorganisms in biological waste water treatment", Biot. and Bioeng., Vol. 15 (1973) p. 1045. The conclusion is that the adhesion of microorganisms by these weak forces is lost when high shearing forces play a part. Since, as said before, in biological processes with highly increased conversion-rates per cubic meter of reactor volume also highly increased shearing forces are necessary, the adhesion of biomass through this kind of forces is not interesting.

(2) Another adhesion of biomass is to a surface by means of slime films and this adhesion is stronger than the adhesion by the above-mentioned weak forces. In practice, this adhesion is well-known and can be seen in processes like (a) Trickle filters M. F. Kong et al., "Practical design equations for trickling filter process", Biot. and Bioeng., Vol. 21 (1979), p. 417, (b) Fluidized bed denitrification J. S. Jeris et al, "high rate biological denitrification using a granular fluidized bed", J. Water Poll. Contr. Fed. Vol. 46 (1974), p. 2118 and Dutch patent application No. 73,08423 and (c) Fluidized bed BOD-reduction J. S. Jeris et al. "Biological fluidized bed treatment for BOD and nitrogen removal", J. Water Poll. Contr. Fed. Vol. 49 (1977), p. 816 and Dutch patent application No. 74,01957.

Also when there is question of adhesion by a slime film, the biomass comes off the carrier when strong shearing forces play a part and it is washed away from the reactor. In the fluidized bed processes (b) and (c), use is made of this phenomenon and air is blown in to loosen the biofilms to prevent blocking of the reactor. Also there is little information about the conditions which are required for the formation of a biomass attached to a carrier. As a general rule, it can be stated that always in a reaction space, a granular carrier is contacted with a continuous liquid stream which contains a sufficiently wide flora of microogranisms and a sufficient amount of nutrients required for the grough and/or preservation for the microorganisms, until a sufficiently thick layer of microorganisms is attached to the carrier.

The carrier material is considered an essential by some people D. W. Levine et al "Optimisation of growth surface parameter in micro carrier culture", Biot. and Bioeng. Vol. 21 (1979), p. 821. In the above-mentioned known processes, wherein use is made of fluidized particles of a carrier with an attached biomass layer, the carrier particles which are seeded with usual bacteria from normal waste water are introduced into a "fluidized bed reactor" and subsequently the carrier is brought to a fluidized condition by an upward stream of waste water wherein before air has been dissolved, a layer of biomass is formed on the carrier particles. However, as said before, the biomass comes off under conditions of high shearing forces.

It is to be inferred, that the present process, i.e. with respect to its feature of maintenance of attached bio-layers once formed and thereby also to its propensity to purify waste waters in general without undue production of excessive biological waste, only functions well in the absence of locally high and indiscriminative shearing forces as provided for by an additional mechanical stirring tool. In this respect it is mentioned, that "Suspended-Sludge-on-Solid Reactor: A New System for the Activated Sludge Process" (by K. Rietema et al in Biotechnology and Bioengineering, Vol. XIII (1971), pages 911–917; published as Communications to the Editor) not only contains an early indication that it may be advantageous to use sludge in an attached state on a suspended carrier, but also contains an early indication, that at least during aerobic COD removal, wherein air or oxygen passed through provides for a substantial level of stirring already, it may not be really necessary to employ energy consuming additional mechanical stirring. That method however, while not incorporating the other characterizing aspects of the present invention, has only been described for excessive sludge producing purification of waste water having a low COD content by only one kind of operation, while using very small lab-scale fermentors and therein a relatively small amount of attached biomass per unit of volume as a consequence of introduction of a relatively very low amount of small-size low-density carrier material per unit of volume, the carrier material having special surface qualities as well.

It is to be added, that for one specified kind of waste water treatment, i.e. for aerobic removal of COD being predestined by nature to produce relatively very much excessive sludge if unchecked, it was found to be possible to refrain from production of excessive sludge to at least a very substantial extent by a purely empirical method of by necessity very simple technology, which process is also characterized by the absence of substantial additional stirring. In that specific process, described in commonly assigned application Ser. No. 404,050 being a continuation of application Ser. No. 181,360 now abandoned and filed two days earlier than the present invention, the desired no-growth condition is reached to at least a very substantial extent after a considerable period of time ranging from several days to a few weeks, without explicit previous separation of adhering from non-adhering species and without explicit matching of the residence time to a value lower than the reciprocal maximum growth rate of the microorganisms involved. While still being able to reach industrially attractive space loads of conversion per day, that advantageous condition can be reached and controlled and has to be controlled regularly by an overall very simple technology, implicating watch-over of the state of attachment by a simple overflow unit of relatively lower height preferably placed on top of the oxidation space by visual insepection, and or by measuring the carbon dioxide content versus the oxygen content in the off gas, whereby then if necessary the residence time can be lowered by changing the flow rate of the waste water.

In relation to this companion application, reference has been made to: British Pat. No. 1,341,107, U.S. Pat. Nos. 4,200,524 and 4,089,148, Japanese Pat. No. 54-107156, and "Stoichiometry of Industrial Biological Wastewater Treatment" by J. H. Sherrard and E. D. Schroeder (30th Ind. Waste Conf. (1975), p. 14–22, Purdue Univ. Lafayette). The patents cited were assessed not to contain sufficiently relevant prior art with regard to this application.

It may be called into question whether it is within reason possible to derive in particular the present invention simple guiding relationship between the residence time and the maximum growth rate of the microorganisms involved from: considerations of mechanical microbial attachment; attempts to formulate mathematically the proceedings of a fermentation process employing attached bio-layers; microbiological experiments with attached bio-layers, such as they are occasionally arising in the scientific literature, for instance in "The Completely Mixed Microbial Film Fermentor" by B. Atkinson et al (Trans. Instn. Chem. Engrs., Vol. 50 (1972), p. 298–216). Apart from the circumstance, that it is held to be impossible to derive such a simple relationship from the above-mentioned information, i.e. in particular with respect to the quite complex equations proposed therein, no information has been presented on the necessity of completely washing out non-adhering microorganisms.

OBJECTS OF THE INVENTION

It is an object of the invention to provide an improved process for producing a biomass attached to a carrier whereby the biomass will not be removed during use.

It is another object of the invention to provide a novel process for the purification of waste water.

These and other objects and advantages of the invention will become obvious from the following detailed description.

THE INVENTION

In a process for the production and maintenance of well-adhering biomass attached to carrier particles capable of decomposing contaminants in waste water containing both well-adhering and non-adhering microorganisms wherein a granular carrier is contacted in a reaction space with a continuous stream of waste water containing both well-adhering and non-adhering microorganisms and nutrients for the growth and the maintenance of the microorganisms in an adherent layer until a sufficiently thick, well-adhering layer of microorganisms is formed and maintained on the carrier, the improvement comprising maintaining the residence time of the waste water in the reaction space lower than the recipocal maximum growth rate of the microorganisms on carrier particles of at least 0.1 mm while generating in the reaction liquid shear forces caused by liquid motion and circulation caused by gas bubbles and washing out of the reaction space all non-adhering microorganisms.

By way of indication it can be expressed in an approximate fashion, that under practical conditions, i.e. with column heights varying from 2 to 25 meters and with specific gravities of carrier material varying from about 2 to 5 g/cm$^3$, the shear forces applied amount to dissipation of mechanical energy of 0.01 to 2.0 kW per cubic meter of reactor liquid when calculated according to an appropriate method.

In an important example, relating to a much practiced treatment of waste water, an aerobic biomass attached to a carrier for removal of COD is produced by using liquids wherein the growth rate is not limited by the concentration of nutrients and by adjusting a residence time of the liquid in the reactor to below 45 minutes.

A considerably advantageous feature of application of the process of this invention is, that in the absence of substantial additional mechanical stirring the firmly attached bio-layers generally can be used subsequently in a continuous uninterrupted fashion without substantial further accrescence of biomass if the residence time of the liquid in the reaction space remains to be kept lower than the reciprocal maximum growth rate of the microorganisms involved. Particularly in cases of purification of waste water, this advantageous feature is related to considerable reduction in the investments of energy, man-power and space as compared with existing processes.

In an investigation of the possibility of attaching biomass to a carrier so that the biomass does not come off even under conditions of high shearing forces, it appeared that the working conditions were critical. First, a test series was started to check whether fluidization per se or the nature of the carrier material were essential for the growth of aerobic active sludge onto a carrier. The tests were carried out in a column reactor with a height of 6 meters and a diameter of 25 cm, the temperature was 40° C. and the pH value was adjusted between 6.5 and 8.0. Air was blown in at the bottom of the column through a star-shaped sparger and the air-input was varied between 0.7 and 19.2 Nm$^3$/h which corresponds to a superficial gas velocity of 0.38–11 cm/s. Under these conditions, the power dissipation was 38–1100 W/m$^3$ and with amounts of air corresponding to a superficial velocity of 2 cm/s and more, the liquid motion in the column was highly turbulent. Waste water was passed through the bottom of the column in an amount of 25 l/h which meant a liquid residence time of 11 hours in the column. The COD concentration of the waste water varied from day to day with as extreme limits 3000 and 1200 mg COD/l. This waste water was previously freed from all possible suspended organic substance.

Subsequently, use was made of the following carrier materials:
river gravel, grain size 0.8–1.2 mm
silver sand, grain size 0.1–0.3 mm
glass ballotini, grain size 0.25–0.32 mm
glass ballotini, grain size 0.1–0.12 mm
active carbon, grain size 0.25–1 mm
Eiffel-lava, grain size 1 mm With each of these carrier materials, tests were made using a large range of fluidization patterns varying from no fluidization at all to good fluidization and each carrier material was tested in the column for 2 or 3 weeks for growth of biomass on the carrier. However, all tests in these series had one disappointing result, namely that no growth of attached active aerobic sludge took place, and therefore it was concluded that the nature of the carrier and the test conditions varying from fluidization to no fluidization are not essential factors for adhesion of active aerobic sludge onto a carrier, but that other factors are important.

Further tests showed that for obtaining a biomass film on a carrier which does not come off under strong shearing forces, it is essential that the residence time of the waste water in the reaction space be kept lower than the reciprocal maximum growth rate of the microorganisms on carrier particles of at least 0.1 mm to maintain the well-adhering layer of microorganisms, while generating in the reaction liquid shear forces caused by liquid motion and circulation caused by gas bubbles, and removing all non-adhering microorganisms from the reaction space. These requirements might possibly be explained in the following way. The raw waste water, which is passed through the reaction space, contains a large number of various microorganisms of which there are some which show adhesive properties to the carrier in the reactor under conditions of high shearing forces which are present in the column, and which are also capable of decomposing the contaminants in the waste water.

By adjusting conditions which give a liquid residence time in the reaction space which is shorter than the reciprocal growth rate of the microorganisms while simultaneously dissipating approximately 0.01–2.0 kW of mechanical energy per cubic meter of reactor liquid to generate sufficiently high shearing forces in the reactor liquid, the non-adhering microorganisms are inhibited to attach and are washed away by the passage of the liquid through the reaction space. Then, the microorganisms, which can adhere to the carrier, are not overgrown with the non-adhering microorganisms and since they attach to the carrier, they cannot be washed away from the column. Also, as the non-adhering microorganisms do not have time to multiply on the substrate, the substrate remains available for consumption by the adhering microorganisms, and as long as the substrate concentration is non-limiting, the adhering microorganisms multiply within the attached bio-layers. The attached bio-layers expand in thickness until the moment arrives, that the substrate concentration has become limiting, whereupon the substrate concentration is only sufficient for maintenance.

The maximum growth rate of the microorganisms generally depends on the type of microorganisms, on the type of substrate, on the temperature and on the substrate concentration in the column. Thus, the microorganisms which play a part in aerobic removal of COD from waste water, as well as denitrifying microorganisms, generally grow rather quick, but most of the various organisms which play a part in anaerobic removal of COD from waste water, as well as nitrifying microorganisms, grow much slower. As known, the maximum growth rate of all microorganisms increases with the temperature according to the Arrhenius-relation.

For the aerobic removal of COD from waste water, it appeared that when the growth rate of the microorganisms is not limited by the concentration of nutrients, in practice such a growth, with a liquid residence time in the reactor of below 45 minutes leads to a carrier with a good adhering layer of biomass. Longer liquid residence time is possible, but not necessary.

If the temperature of the reactor contents is 30°–50° C., the residence time of the liquid for forming a layer of aerobic COD-removing biomass onto the carrier, is preferably adjusted to at most 30 minutes. A longer residence time then does not provide for a better result, but is less economical. When producing an anaerobic COD-removing biomass onto a carrier, the residence time is suitable between 1 hour and 4 hours and if the temperature of the reactor contents is 30°–50° C., preferably between 2 hours and 3 hours.

Upon dividing the one-step anaerobic treatment of waste water into a first acetogenic fermentation, wherein a major part of contaminants prevailing in industrial waste waters is decomposed into a mixture of lower fatty acids, e.g. acetic acid and butyric acid, and a second methanogenic treatment converting those fatty acids into methane and carbon dioxide, both fermentations can be carried out at individually more suited conditions, e.g. at an individually more appropriate pH range. This then results in the possibility of shorter residence times for both treatments as compared with the residence time in an one-step anaerobic COD-removing purification. When producing methanogenic biomass on carrier at 30°–50° C., the residence time of the liquid in the reactor suitably is 30 to 90 minutes.

Adjusting the liquid residence time in the reaction space in principle can be obtained by varying the amount of liquid passed through the reactor. However, in certain cases practical limits are set hereto. For instance, when producing an aerobic COD-removing biomass on a carrier, not only a relatively short residence time should be adjusted, but also sufficient oxygen should be available for the conversion of the COD.

Theoretically, about 1.0 kg of oxygen per kg COD is required and preferably while producing biomass for aerobic removal of COD carrier at least such an amount of air and/or oxygen is introduced so that per kg COD coming into the reaction space, 0.8–1.6 kg is transferred to the reactor liquid. However, the amount of air and/or oxygen, which can be introduced into the reaction space, is limited to a maximum.

Therefore, if the available waste water is highly contaminated (has a high COD) as is often the case with industrial waste water, especially from industries where biological materials are treated or biological processes are used, it is not easy to vary the amount of liquid passed through the reactor, but considering the maximum amount of air and/or oxygen which can be passed through the reactor, the waste water should often be diluted so that the COD reaches a suitable value. For a practical aerobic COD-removing reactor wherein air is introduced, while the liquid residence time in the reactor is 15–30 minutes, e.g. a COD of the waste water between 200 and 500 mg/l is suitable. If the air is replaced by oxygen, then the COD of the waste water can be about 5 times as high, i.e. between 1000 and 2500 mg/l.

To obtain a smooth course of the process, it is desired that no forming takes place in the reactor and therefore, an antifoaming agent can be added, if necessary. Any known antifoaming agent like silicones, e.g. glycolpolysiloxane, methylphenylpolysiloxane, liquid polydimethylsiloxanes, propyleneglycol, triethanolamine, higher alcohols or polyoxyalkylenes are suitable.

The process of the invention can be used for the production of high amounts per cubic meter of reactor volume of all kinds of biomass attached to a carrier, e.g. biomasses as are applied in the biological purification of waste water, aerobic biomass, anaerobic biomass, nitrifying biomass and denitrifying biomass as well as biomasses which form a desired metabolic product which at higher concentration inhibits its own production rate, like biomass for the production of alcohol.

The biomass on a carrier which are obtained by the process according to the invention allow a considerably higher concentration of attached biomass than is used in known processes until now.

A considerably advantageous feature of application of the process of this invention is, that in the absence of substantial additional mechanical stirring the firmly attached bio-layers in general can be used subsequently in a continuous uninterrupted fashion without substantial further accrescence of biomass if the residence time of the liquid in the reaction space remains to be kept lower than the reciprocal maximum growth rate of the microorganisms involved. Particularly in case of purification of waste water, this advantageous feature is related to considerable reduction in the investments of energy, man-power and space as compared with existing processes.

BRIEF DESCRIPTION OF THE DRAWINGS

The invention is further elucidated by examples wherein use was made of a column shown in FIG. 1 of the enclosed drawings. This figure shows a column 1 which at the top is provided with a settling degassing member 2 which is provided with an overflow 3 and waste gas pipe 4. Also, a supply 5 is present by which, if necessary, the anti-foaming agent can be dosed. Waste water is introduced at the bottom of the column at point 6 and also air is shown in through an eight-foot star-shaped sparger via line 9. Tap water can be introduced into the column via point 7 or 8 and a sand trap (not shown) is placed behind the column in the outlet for the treated water.

In the examples, the dissipation of mechanical energy is calculated in an approximative fashion with the help of seven equations adapted from or directly derived from the following literature references:

Figure 1:
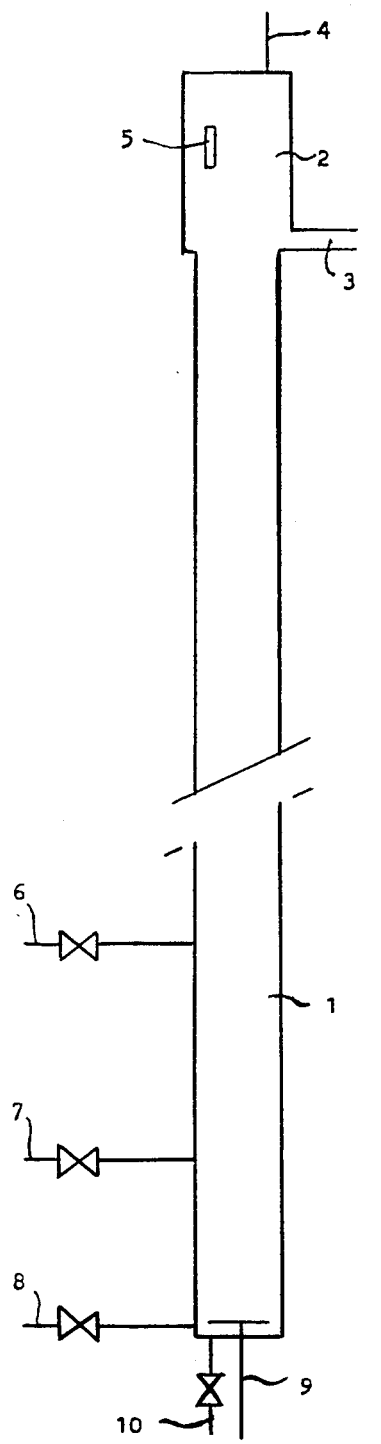

Ref. 1. J. J. Heijnen. K. van 't Riet, Mass transfer, mixing and heating transfer phenomena in low viscous bubble column reactors Fourth European Conference on mixing April. 27-29, 1982 p. 195 Noordwijkerhout, The Netherlands.

Ref. 2. K. Rietema, S. P. P. Ottengraf, Laminar liquid circulation and bubble streat formation in a gas-liquid system Trans. Instn. Chem. Engrs. 48 (1970), T54.

Ref. 3. R. B. Bird, W. E. Stewart, E. N. Lightfoot, Transport Phenomena John Wiley and Sons N.Y. (1960), p. 214

The dissipation of mechanical energy in fluidized beds is the result of the passage of liquid through the fluidized bed, as well as of the flow of gas through the bed. For approximative calculation of this energy dissipation, the following data are needed:

1. The superficial gas velocity in the fluidized bed is indicated by $v_{sg}$ (m/s).

For aerobic cases $v_{sg}$ is given by:

$$v_{sg} = Q_g/A \qquad (1)$$

wherein $Q_g$ (m$^3$/s) is the output of air related to normal conditions, i.e. to 0° C. and 1 bar, and A (m$^2$) is the cross section of the fluidized bed. For $Q_g$ is therefore taken the maximal $Q_q$ prevailing in the top of the reactor, where the pressure is approximatively atmospheric.

For anaerobic case, $v_{sg}$ is given by:

$$v_{sg} = \frac{Q_g' \cdot A \cdot H}{24.3600 \cdot A} = 1.16 \times 10^{-5} Q_g' H \qquad \text{equation (1a)}$$

wherein H (m) is the height of the fluidized bed and $Q_g'$ is the produced volume of gas per volume of reactor per day.

It emerges from equation (1a), that $v_{sg}$ increases proportionally with H. For $Q_g'$ is taken the maximal value, because this represents the highest energy dissipated to which the bio-layers are exposed.

2. The superficial liquid velocity in the fluidized bed is indicated by $v_{sL}$ (m/s). This velocity follows in a simple way from the introduced amount of waste water, indicated by $Q_L$ (m³/s), while taking into account the recycled waste water, indicated by $Q^R L$ (m³/s).

The superificial liquid velocity is thus given by:

$$v_{sL} = \frac{Q_L + Q^R L}{A} \qquad \text{equation (2)}$$

3. The density of the fluidized bed is indicated by $\rho_B$ (kg/m³). Since the fluidized bed consists of liquid and overgrown particles, the density of the bed is a function of the concentration of the carrier material, indicated by $C_c$(kg/m³) and of the specific weight of the carrier material indicated by $\rho_c$. While assuming that the density of the bio-layers equals the density of water, which is 1000 kg/m³, the density of the fluidized bed is given by:

$$\rho_B = \left[ 1000 \times \left( 1 - \frac{C_c}{\rho_c} \right) + C_c \right] \qquad \text{equation (3)}$$

4. The liquid hold-up of the fluidized bed is indicated by $\epsilon_L$. The liquid hold-up in the fluidized bed is a function of the gas hold-up, indicated by $\epsilon_g$, of the carrier volume and of the bio-layer volume. The gas hold-up follows from the gas velocity, and according to ref.1 the following correlation can be applied by way of a rough approximation:

$$\epsilon_g = 0.6(v_{sg})^{0.7} \qquad (4)$$

If the gas hold-up has not been measured in practice, this correlation can be employed for an estimation of the actually prevailing gas hold-up. The volume of the bio-layer is directly proportional to the biomass concentration in the fluidized bed, indicated by $C_x$ and expressed in kg D.M./m³ (D.M. stands for dry matter). It has been found empirically that 150 kg D.M. corresponds to 1 m³ of bio-layer.

The liquid hold-up is then given by:

$$\epsilon_L = 1 - \frac{C_c(1 - \epsilon_g)}{\rho c} - \frac{C_x(1 - \epsilon_g)}{150} - \epsilon_g \qquad \text{equation (5)}$$

The appearance in equation (5) of the term $(1 - \epsilon_g)$ is a consequence of measuring $C_c$ and $C_x$ with the help of a sample taken from the fluidized bed, whereby that sample of course has lost its gas fraction.

5. The energy dissipation per unit of liquid volume, originating from the flow of gas, is indicated by $(P/V)^g$ (W/m³) (ref.2,3). The energy originating from the flow of gas is given by:

$$(P/V)^g = \frac{\rho_B g \, v_{sg} (1 - \epsilon_g)}{\epsilon_L} \qquad \text{equation (6a)}$$

wherein g (m/sec²) is the gravitational acceleration constant.

6. The energy dissipation per unit of liquid volume, originating from the flow of liquid, is indicated by $(P/V)^L$ (W/m³) (ref. 2,3). The energy originating from the flow of liquid is given by:

$$(P/V)^L = \frac{(\rho_B - 1000)g \, v_{sL}(1 - \epsilon_g)}{\epsilon_L} \qquad \text{equation (6b)}$$

7. The total energy dissipated in the fluidized bed per unit of liquid volume is indicated by (P/V) (W/m³). The total energy dissipated per unit of volume is given by:

$$(P/V) = (P/V)^g + (P/V)^L \qquad (7)$$

The equations (6a) and (6b) are derived from ref. 2. They can be derived explicitly while making use of Bernoulli's Law (see ref. 3) and while assuming that in the case of liquid flow, liquid has a density of 1000 kg/m³ (the approximate density of pure water) and that in the case of gas flow, gas has a density zero.

It must be stipulated that for any application of the process of this invention it should be taken into account that the calculated total amount of energy dissipation is according to equations (3) and (5) always dependent on the specific gravity of the carrier material, while furthermore in anaerobic cases there also prevails dependence on the height of the fluidized bed according to equation (1a). Furthermore, although the method for calculation of energy employed in this invention is believed to be substantially appropriate, the selection of a calculation method intrinsically remains to be a somewhat ambiguous aspect influencing any numeral delimitation of energy dissipation boundaries.

In the following examples there are described several preferred embodiments to illustrate the invention. However, it should be understood that the invention is not intended to be limited to the specific embodiments.

EXAMPLE 1

Use was made of the column of FIG. 1 which had a height of 6 m and a diameter of 25 cm and the settling degassing member had a height of 75 cm. After adding 40 kg of silver sand with a grain size of 0.1–0.3 mm to the column, the column was filled with tap water. Then waste-water was introduced in an amount of 25 l/hour at point 6 and at point 8, tap water in an amount of 330 l/hour was introduced in the first test and of 660 l/hour in the second test was introduced. The pH of the liquid in the column was adjusted to a value between 6.5 and 8.0 and the temperature in the column was maintained at 40° C. by steam injection at point 10. The amount of air which was introduced in a first test was 0.71 Nm³/h (corresponding to 45 W/m³) and in a second test 4.2 Nm³/h (corresponding to 273 W/m³). The $\epsilon_L$-values were 0.92 and 0.76 respectively. The $(P/V)^L$ energies were calculated to 1.6 W/m³ and 3.3 W/m³ respectively. The total amount of energy dissipated in the first test therefore was 45+1.6=47 W/m³ and in the second test 273+3.3=276 W/m³. The residence times were 49 minutes and 26 minutes respectively. In both tests, a considerable growth of biomass on the sand was observable within a few days.

Figure 2:
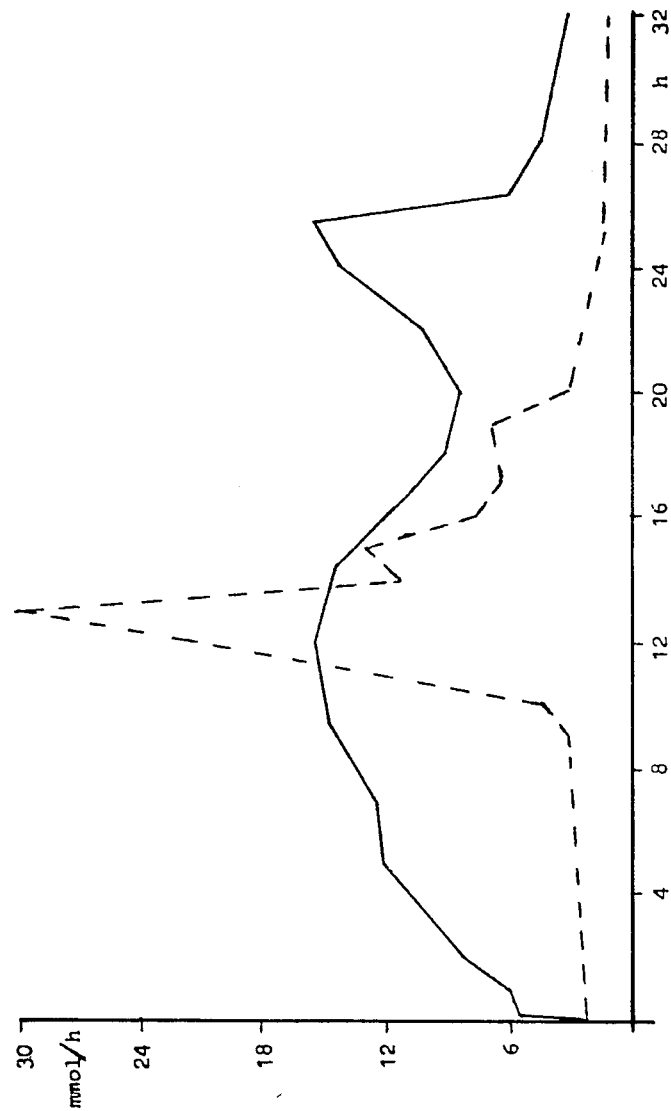
Figure 3:
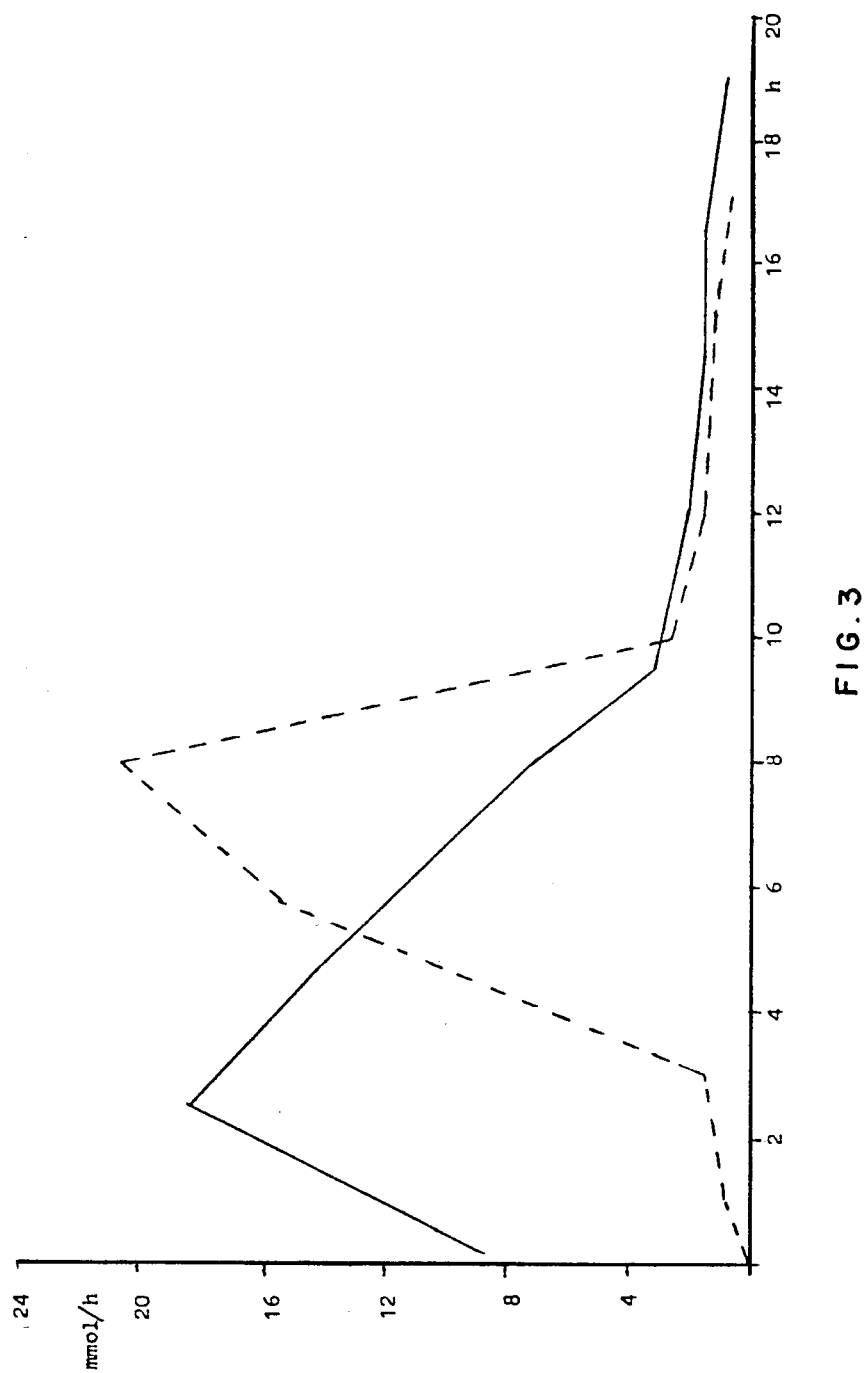
Figure 4:
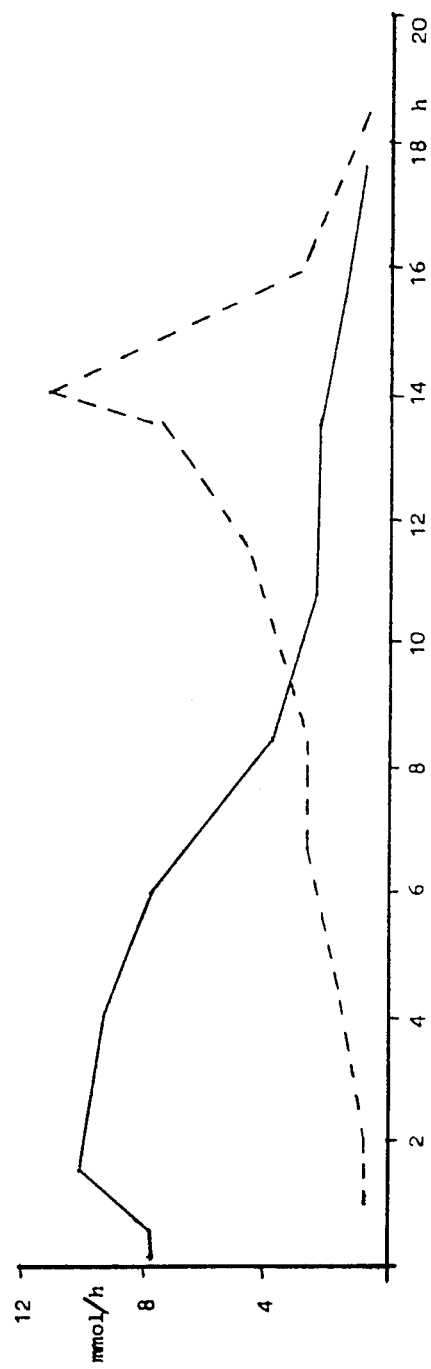

At several times, samples of this sand grown with biomass were taken from the column (sample a after the first day of test 1 and samples b and c after the first and second day of test 2) and were thoroughly washed with clean water. Thereafter, a test was effected with the samples in an Eschweiler fermentor of 6 liters to determine the activity of the sand grown with biomass wherein 25 ml of sample a and 20 ml of sample b or 20 ml of sample c, respectively, were brought in the fermentor. The Eschweiler fermentor was filled each time with 3 liters of waste water and air was passed through in an amount of 200 l/hour. The impeller was stirred at a velocity of 200 rpm with sample a, and with a velocity of 300 rpm for samples b and c and the temperature was always 40° C. The results are shown in the graphs of FIGS. 2–4 which show the amount of oxygen consumption in mmol/h against the reaction time in hours. The solid curve indicates the oxygen consumption as a function of time for the fermentor which was seeded with biomass attached to sand. The dashed curve indicates the oxygen consumption for the fermentor which was not seeded with biomass attached to sand (blank). The oxygen consumption in the blanks was the result of the growth of bacteria which are naturally present in the waste water.

The tests with a fermentor wherein biomass attached to sand was used show immediately a high oxygen consumption with respect to the blank-tests. Also, the areas of the curves for the blank tests and for the tests using biomass attached to carrier are roughly equal, or in other words, total oxygen consumption is roughly equal. This means, that with biomass attached to sand, a similar COD reduction of the waste water is possible as with suspended active sludge.

The samples of biomass attached to sand were also bacteriologically analyzed and from these analysis, it appears that large amounts of microorganisms were present on the sand. From visual observation, it appeared that sand grains with a diameter of 200 μm had obtained a diameter of about 300 μm by the attached biomass. In other words, the bio-film was about 500 μm thick and for this film thickness, no diffusion limitation is to be expected.

In the following table, some analysis results have been collected of the samples of active aerobic sludge on the carrier and all data are based on 1 liter of settled sand grains with bio-films in water. Silver sand with a grain size of 0.1 to 0.3 mm, a density of 2.6 g/cm³ and a bulk density of 1.65 g/cm³ was used.

bio-film which corresponds reasonably with this visual observation.

From the graphs 2–4, it follows that the sand with bio-film had an oxygen uptake capacity of about 9 mmol/h for 20 ml of sand with bio-film and for the biomass, this means an oxygen uptake rate of $$\frac{9}{0.020 \times 75} = 6 \text{ mmol } O_2/g.h.$$

This is in reasonable conformity with the maximum oxygen uptake capacity of suspended sludge of 8 mmol $O_2/g$. hour found in other tests and confirms the absence of diffusion-limitation. Also, it follows from the measured N- and COD-concentrations of the table that all dry substance consists of organic material. The ratio between bio-film volume and volatile dry substance is also in agreement with this conclusion. Furthermore sample a was only tested after keeping it for two days at 5° C. so that it seems probable that active sludge attached to a carrier can be preserved for a longtime. From a settling test, it appeared that the settling rate of the sand grains with bio-film was about 50 m/hours.

EXAMPLE 2

Use was made of a column of FIG. 1 with a height of 6.5 m and a diameter of 25 cm (useful volume 300 l) and 80 kg of silver sand (particle size 0.1–0.3 mm) were introduced into the column. 40 l/hour of waste water with a COD of 6000 mg/l were introduced via point 6, and 760 l/hour of tap water were introduced via point 7, COD of the mixture was 300 mg/l with a residence time in the reactor of ⅔ hours 20 Nm³/hour of air were introduced via point 9 corresponding to an air velocity based on the cross section of the column of 11 cm/s. The specific gravity of the sand used was 2600 kg/m³. The concentration of carrier material $C_c$ was 210 kg/m³. The gas hold-up $\epsilon_g$ was estimated to 0.13. The biomass concentration $C_x$ was 15 kg/m³. The liquid hold-up was calculated to 0.715. Since the calculated $(P/V)^g$ amount to 1480 W/m³ and the $(P/V)^L$ to 7 W/m³, the total amount of energy dissipated was 1.49 kW/m³. The residence time in operation was 24 minutes.

After 1 week, the sand was overgrown with a layer of biomass and a stationary condition was established. Analysis of a sample of the sand with bio-layer showed that on 1 liter of settled sand grains with a bulk density 1.65 g/cm³ and overgrown with bio-layer, 50 g of biomass (calculated as dry substance) were present and the thickness of the bio-film was 40 μm. The amount of

TABLE

ANALYSIS RESULTS OF BIOMASS ATTACHED TO SAND

| Sample | Density | g ash/l | g of volatile dry substance per l | N (g/l) | COD (g/l) | P (g/l) | cm³ biofilm per l | ratio biofilm volume to volatile dry substance cm³/g | volume ratio of biofilm to sand |
|---|---|---|---|---|---|---|---|---|---|
| a | — | 769 | 95 | 5.00 | — | 2.0 | 364 | 4.0 | 1.23 |
| b | 1.59 | 801 | 61 | 7.16 | 73.3 | 21.8 | 352 | 5.9 | 1.14 |
| c | 1.66 | 610 | 75 | 8.30 | 111.9 | 6.1 | 425 | 5.67 | 1.81 |

From the table, it appears that 1 liter of sand with bio-film contains about 75 g of biomass dry substance and from the volume ratio of bio-film to sand of 1.2–1.8, it can be calculated that a sand grain with bio-films has 1.3–1.4 times the diameter of the sand grain without a bio-film. At an average grain diameter of 200 μm, this means a diameter of 270 μm for the sand grain with a biomass in the reactor (calculated as dry substance) was 15 g/l. With this biomass concentration, waste water with a COD of 300 mg/l under the above mentioned conditions gave a COD decrease of 70% at a COD-load of 20 kg/m³ (reactor space) day. The biomass attached to the carrier remained unaltered and no further growth of biomass took place and washing away of biomass was not noticed.

EXAMPLE 3

Use was made of a column of FIG. 1 with a height of 4 m and a diameter of 7.6 cm (useful volume of 18 l) and a test was carried out for the formation of an anaerobic biomass on a carrier in this reactor. 20.6 kg of silversand with a particle size of 0.1-0.3 mm, a density of 2.6 g/cm$^3$ and a bulk density of 1.65 g/cm$^3$ were introduced into the reactor. Waste water with a COD of 6000 mg/l was introduced via point 6 in an amount of 7.5 l/hour (liquid residence time 2.4 hour since the recirculation rate was 50 l/hour) which corresponded to a COD load of 60 kg COD/m$^3$ day. The pH in the reactor varied between 7-8 and temperature was maintained at 40° C. Gas was developed by anaerobic conversion of COD. After 6 weeks, the sand was overgrown with a layer of biomass and a stationary condition was obtained.

Under the above mentioned conditions, a COD decrease of 60% was obtained after reaching the stationary condition and gas development was 15 m$^3$/m$^3$ reactor per day and the CH$_4$ content of that gas was 70%.

The total amount of energy dissipated with 111 W/m$^3$, being the sum of a (P/V)$^g$ of 35 W/m$^3$ and a (P/V)$^L$ of 76 W/m$^3$. The calculations were made with the help of the following data: $C_c$=1144 kg/m$^3$, $C_x$=36 kg/m$^3$ as estimated from COD-removal efficiency, $\epsilon_g$=0.004 and $\epsilon_L$=0.32.

EXAMPLE 4

For production of aerobic COD-removing biomass on silver sand on pilot plant scale, the fermentation was performed at 40° C., while the pH of the liquid in the column was maintained between 6.0 and 8.0. The influent contained a COD concentration of about 300 mg/l and the residence time was 25 minutes. The COD removal efficiency was 70%.

The starting data needed for the calculation are: A=0.049 m$^2$, H=6.5 m, $Q_g$=8.1 Nm$^3$/hour=23.10$^{-3}$ m$^3$/s, $Q_L$=30 l/h of waste water+720 l/h of tap water=0.21.10$^{-3}$ m$^3$/s, $Q^RL$=0, $\epsilon_g$=0.13, .$C_c$=100 kg/m$^3$, $\rho_c$=2600 kg/m$^3$ and biomass $C_x$=11 kg/m$^3$.

By means of equations 1-5 the values calculated for $v_{sg}$, $v_{sL}$, $\rho B$ and $\epsilon_L$ were:

$$v_{sg} = 23.10^{-3}/0.049 = 0.47 \text{ m/s}$$
$$v_{sL} = 0.21.10^{-3}/0.049 = 4.3.10^{-3} \text{ m/s}$$
$$\rho_B = 1061 \text{ kg/m}^3$$
$$\epsilon_L = 1 - \frac{100}{2600}(0.87) - \frac{11}{150}(0.87) - 0.13 = 0.77$$

While making use of equations 6a and 6b, these values resulted in 552 W/m$^3$ for the energy dissipated by the flow of gas and 3 W/m$^3$ for the energy dissipated by the liquid flow. The total amount of energy dissipated therefore was 0.555 kW/m$^3$.

EXAMPLE 5

For production of nitrifying (aerobic) biomass on marl on a pilot plant scale, the fermentation was performed at 37° C., while the pH in the column was allowed to vary between 7.0 and 9.0. The influent contained 200 mg of NH$_3$-N/l. The microbial flora involved was acquired from natural abundance and the residence time was 4.01 hours. The nitrification efficiency reached was 50%. The starting data needed for the calculations are: A=0.0314 m$^2$, H=12.8 m, $Q_g$=3.4 Nm$^3$/h=0.94.10$^{-3}$ m$^3$/s, $Q_L$=0.1 m$^3$/h=0.28.10$^{-4}$ m$^3$/s, $Q^RL$=0.8 m$^3$/h=2.22.10$^{-4}$ m$^3$/s, $C_c$=75 kg/m$^3$ and $\rho_c$=2300 kg/m$^3$. The biomass concentration $C_x$ was not known.

By means of the equations 1-5 and the data given above, the following values were calculated for $v_{sg}$, $v_{sL}$, $\epsilon_g$, $\rho_B$ and $\epsilon_L$:

$$V_{sg} = 0.03 \text{ m/s}$$
$$v_{sL} = 0.008 \text{ m/s}$$
$$\epsilon_g = 0.6 \times (0.03)^{0.07} = 0.051$$
$$\rho_B = 1042 \text{ kg/m}^3$$
$$\epsilon_L = 1 - \frac{75}{2300}(0.949) - 0.051 = 0.92$$

While making use of equation 6a and 6b, these values resulted in 316 W/m$^3$ for the energy dissipated by the flow of gas and 3.4 W/m$^3$ for the energy dissipated by the liquid flow. These values for (P/V)$^g$ and (P/V)$^L$ are minimal since in the application of equation 5 the third term had to be ignored, so that the actual liquid hold-up factor $\epsilon_L$ was smaller than 0.92. The total amount of energy as calculated by equation 7 is in fact therefore somewhat greater than 319 W/m$^3$.

EXAMPLE 6

For production of nitrifying biomass on silver sand on lab scale, the temperature was 37° C. and the pH was 7.0-9.0. The influent contained 250 mg NH$_3$-N/l and the residence time was 1.63 hours. The nitrification efficiency was 70%.

The starting data needed for the calculation are: A=0.00071 m$^2$, H=1.15 m, $Q_g$=122 l/hours=0.34.10$^{-4}$ m$^3$/s, $Q_L$=0.5 l/hour=1.39.10$^{-7}$ m/s, $Q^RL$=28 l/hour=77.8.10$^{-7}$ m$^3$/s, $C_c$=50 kg/m$^3$ and $\rho_c$=2600 kg/m$^3$. The biomass concentration $C_x$ was not known. The calculation with these data and the equations 1-5 resulted in: $v_{sg}$=0.048 m/s, $v_{sL}$=0.011 m/s, $\epsilon_g$=0.072, $\rho_B$=1031 kg/m$^3$ and $\epsilon_L$=0.91.

As in Example 5, not knowing $C_x$ resulted in the use of a too large $\epsilon_L$ value, so that the 495 W/m$^3$ for the gas flow and the 3.4 W/m$^3$ for the liquid flow are caluclated somewhat too low. The same holds for the total amount of energy dissipated whch is somewhat more than 498 W/m$^3$.

EXAMPLE 7

For production of denitrifying (anaerobic) biomass on 1 mm grit on pilot plant scale using microbial flora acquired from natural abundance, the reduction agent employed was inorganic sulfide (170 mg sulfide per liter), which was completely oxidized to sulfate. The off-gas was 80% nitrogen and the concentration of nitrate in the influent was maintained at 225 mg/l NO$_3$-N per liter. The temperature was 37° C. and the pH was 7.85. Residence time was 2.66 hours.

The starting data needed for the calculation are: A=0.0314 m$^2$, H=12.7 m, $Q_g$=1 m$^3$/day=1.16$^{-5}$ m$^3$/s, $Q_L$=0.15 m$^3$/hour=4.16.10$^{-5}$ m$^3$/s, $Q^RL$=0.80 m$^3$/hour=22.2.10$^{-5}$ m$^3$/s, $C_c$=120 kg/m$^3$, $\rho_c$=2600 kg/m$^3$ and biomass $C_x$=30 kg/m$^3$.

The calculations with these data and the equations 1-5 resulted in: $v_{sg}$=0.37.10$^{-3}$ m/s, $v_{sL}$=8.4.10$^{-3}$ m/s, $\epsilon_g$=0.0024, $\rho_B$=1074 kg/m$^3$ and $\epsilon_L$=0.75.

Insertion of these values in equation 6a and 6b gave: (P/V)$^g$=5.2 W/m$^3$ and (P/V)$^L$=8.1 W/m$^3$. The total amount of mechanical energy dissipated therefore amounted to 13.3 W/m³.

EXAMPLE 8

For production of acetogenic (anaerobic) biomass on silver sand using industrial waste water containing 4.5 g/l of COD on pilot plant scale, the fatty acid mixture was produced with 65% efficiency on COD-basis at 37° C. and pH 6.0-7.0. Since this type of anaerobic fermentation produces a relatively small amount of gas, the methane concentration in the off-gas, which amounted to 50%, indicated that the microbial flora acquired from natural abundance contained a relatively small fraction of methanogenic microorganisms. The residence time was 1.38 hours.

The starting data needed for the calculation are: $A=0.2$ m², $H=18$ m, $Q_g=30$ m³/day$=8.3$ m³/s, $Q_L=2.6$ m³/hour$=0.72.10^{-3}$ m³/s, $Q^R L=0.4$ m³/hour$=0.11.10^{-3}$ m³/s, $C_c=200$ kg/m³, $\rho_c=2600$ kg/m³ and biomass $C_x=25$ kg/m³.

The calculations with these data using the equations 1-5 resulting in: $v_{sg}=1.75.10^{-3}$ m/s, $v_{sL}=4.15.10^{-3}$ m/s, $\epsilon_g=0.007$, $\rho_B=1123$ kg/m³ and $\epsilon_L=0.75$.

Insertion of these values in eugations 6a and 6b gave: $(P/V)^g=25.5$ W/m³ and $(P/V)^L=6.7$ W/m³.

The total amount of mechanical energy dissipated therefore was 32 W/m³.

EXAMPLE 9

For production of methanogenic (anaerobic) biomass on zirkonic sand in a pilot plant fermentor, the influent containing a fatty acid concentration of 100-2500 mg/l came from an anaerobic acetogenic treatment of industrial waste water and the fatty acid removal efficiency was 70%. The methane content of the off-gas was 75%. Temperature 37° C., pH 6.8-7.5. The residence time was 71 minutes.

The starting data needed for the calculation of the mechanical energy dissipated are: $A=0.049$ m², $H=6$ m, $Q_g=6$ m³/day$=6.9.10^5$ m³/s $Q_L=0.25$ m³/hour$=6.9.10^{-5}$ m³/s, $Q_L^R=1.50$ m³/hour$=41.7.10^{-5}$ m³/s, $C_c=1000$ kg/m³, $\rho_c=4800$ kg/m³ and the biomass concentration $C_x$ was estimated to be about 30 kg/m³ on account of the methane production and the methane-producing activity of the biomass.

With these data, the values of the parameters for the energy calculations were obtained with the help of equations 1-5: $v_{sg}=6.9.10^{-5}/0.049=1.4.10^{-3}$ m/s, $v_{sL}=(6.9+41.7).10^{-5}/0.049=9.9.10^{-3}$ m/s, $\epsilon_g=0.6.(1.4.10^{-3})^{0.7}=0.006$, $\rho_B=1792$ kg/m³ and $\epsilon_L=1-(1000/4800)$ $(0.994)-(30/150)$ $(0.994)-0.006=0.59$.

Insertion of these values in the equations 6a and 6b resulted in: $(P/V)^g=42$ W/m³ and $(P/V)^L=129$ W/m³. According to equation 7, the total amount of energy dissipated in the liquid per unit of volume was approximately 171 W/m³.

EXAMPLE 10

For production of methanogenic (anaerobic) biomass on silver sand in a pilot plant fermentor, the influent contained a fatty acid concentration of 1000-2500 mg/l and the fatty acid removal efficiency was greater than 90%, the methane content of the off-gas was 75% and the temperature was 37° C. and the pH was 6.8-7.5. The residence time was 59 minutes.

The starting data are: $A=0.049$ m², $H=6$ m, $Q_g=11$ m³/m³ day$=1.27.10^{-4}$ m³/s, $Q_L=0.3$ m³/h$=8.3.10^{-5}$ m³/s, $Q^R L=0.05$ m³/hour$=1.39.10^{-5}$ m³/s, $C_c=400$ kg/m³, $\rho_L=2600$ kg/m³ and biomass $C_x=40$ kg/m³.

The subsequent calculations of the values of the parameter resulted in: $v_{sg}=2.6.10^{-3}$ m/s, $v_{sL}=1.98.10^{-3}$ m/s, $\epsilon_g=0.01$, $\rho_B=1246$ kg/m³ and $\epsilon_L=0.57$.

Therefrom it was calculated that $(P/V)^g$ amounted to 55 W/m³ and that $(P/V)^L$ was approximately 8.3 W/m³. The total amount of mechanical energy dissipated in the liquid per unit of volume therefore was about 63 W/m³. It is to be remarked that the difference in energy the dissipated between the experiments of this example and the preceeding example is due in part to the considerably greater specific gravity of zirkonic sand as compared with silver sand.

EXAMPLE 11

For production of methanogenic biomass on silver sand in a lab scale fermentor, the influent fatty acid concentration was 1000-1500 mg/l and fatty acid removal efficiency was greater than 95% with methane content in off-gas of 75%. The temperature was 37° C. and the pH was 6.8-7.5. Residence time was 48 minutes.

The starting data were: $A=0.0078$ m², $H=2.5$ m, $Q_g=27$ l/hour$=33$ m³/m³ day$=7.5.10^{-6}$ m³/s, $Q_L=25$ l/hour$=6.9.10^{-6}$ m³/s, $Q^R L=100$ l/hour$=27.6.10^{-6}$ m³/s, $C_c=30$ kg/m³, $\rho_c=2600$ kg/m³ and biomass $C_x=40$ kg/m³.

The subsequent calculation of the values of the parameters resulted in: $v_{sg}=0.96.10^{-3}$ m/s, $v_{sL}=4.4.10^{-3}$ m/s, $\epsilon_g=0.005$, $\rho_B=1018$ kg/m³ and $\epsilon_L=0.71$.

Therefrom it was calculated that $(P/V)^g$ and $(P/V)^L$ amounted to approximately 13.4 and 1.1 W/m³ respectively. The total amount of mechanical energy dissipated in the liquid per unit of volume therefore was about 14.5 W/m³.

It is to be remarked that the difference in energy dissipated between the experiments of this example and the preceding example is primarily due to the difference in column height.

Various modifications of the process of the invention may be made without departing from the spirit or scope thereof and it is to be understood that the invention is to be limited only as defined in the appended claims.

What I claim is:

1. In a process for the start up and operation of a fluidized bed reactor for the production and maintenance of well-adhering biomass attached to carrier particles capable of decomposing contaminants without sludge production in waste water containing both well-adhering and non-adhering microorganisms wherein granular carrier particles of at least 0.1 mm and with a specific gravity of 2 to 5 g/ml are contacted in a reaction space with a continuous upwardly flowing stream of waste water containing both well-adhering and non-adhering microorganisms and nutrients for the growth of the microorganisms in an adhering layer until a sufficiently thick, well-adhering layer of microorganisms is formed on the carrier, the improvement comprising maintaining the residence time of the waste water in the reaction space lower than the reciprocal maximum growth rate of the microorganisms on carrier particles while generating in the waste water in the reaction space shear forces caused by liquid motion and circulation and caused by gas bubbles only wherein the mechanical energy dissipation is approximately 0.01 to 1.5 kw per m³ of reaction liquid thereby washing out of the reaction space all non-adhering microorganisms by the passage of waste water through the reaction space while the thickness of the well-adhering layer remains constant on the carrier which remains in the reaction space.

2. The process of claim 1 in the production of aerobic biomass for removal of COD attached to a carrier using waste water, the residence time of the waste water in the reactor is less than 45 minutes.

3. The process of claim 2 wherein the residence time is at most 30 minutes at a temperature of 30°–50° C.

4. The process of claim 1 wherein the residence time of the waste water in the reactor in the production of anaerobic biomass for removal of COD attached to a carrier is between 1 hour and 4 hours.

5. The process of claim 4 wherein the residence time is 2–3 hours at a temperature of 30°–50° C.

6. The process of claim 1 wherein the residence time of the waste water in the reactor is between 30 and 90 minutes at 30° to 50° C. during production of methanogenic biomass attached to carrier to remove fatty acids produced in a first anaerobic acetogenic treatment of waste water.

7. The process of claim 1 for production of aerobic biomass for removal of COD attached to a carrier wherein an amount of air and/or oxygen is introduced equivalent to 0.8–1.6 kg of oxygen per kg of COD in the waste water in the reaction space.

8. The process of claim 1 for production of aerobic biomass attached to a carrier for the oxidation of organic carbonaceous substrate in waste water wherein the residence time of the waste water in the reactor is between 0.2–10 hrs.

9. The process of claim 1 wherein the waste water residence time is 0.5–2 hrs at temperatures of 30°–60° C. and easily metabolizable substrates are used.

10. The process of claim 8, wherein the waste water residence time is 2–10 hrs at temperatures of 10°–30° C. and difficultly metabolizable substrates are used.

11. The process of claim 1 for the production of aerobic biomass attached to a carrier for the oxidation of N-compounds in waste water, wherein the residence time of the waste water in the reactor is between 1–5 hrs.

12. The process of claim 1 for production of denitrifying biomass attached to a carrier for the reduction of $NO_3$- to $N_2$ gas, while using waste water wherein the residence time of the waste water is between 0.2–10 hrs.

13. The process of claim 12 wherein the waste water residence time is 0.5–2 hrs at temperatures of 30°–60° C. and an easily metabolizable electron donor is used.

14. The process of claim 12 wherein the waste water residence time is 2–10 hrs at temperatures of 10°–30° C. and a difficultly metabolizable electron donor is used.

15. The process of claim 1 for production of anaerobic biomass attached to a carrier for the production of lower volatile fatty acids from organic compounds in waste water wherein the residence time of the waste water is between 1–15 hours.

16. The process of claim 15 wherein the waste water residence time is between 1–4 hrs at temperatures of 30°–60° C. and at moderate concentrations of 1–10 g/l COD as organic substrate in the waste water.

17. The process of claim 15 wherein the waste water residence time is between 4–15 hrs at temperatures of 10°–30° C. and at concentrations of 10–60 g/l COD as organic substrate in the waste water.

18. The process of claim 1 for production of anaerobic biomass attached to a carrier for the conversion of lower volatile fatty acids in waste water to $CH_4/CO_2$ wherein the residence time of the waste water is between 1–24 hours.

* * * * *